(12) United States Patent
Gombotz et al.

(10) Patent No.: US 9,518,111 B2
(45) Date of Patent: *Dec. 13, 2016

(54) COMPOSITIONS COMPRISING A P75 TUMOR NECROSIS FACTOR RECEPTOR/IG FUSION PROTEIN

(71) Applicant: Immunex Corporation, Thousand Oaks, CA (US)

(72) Inventors: Wayne Richard Gombotz, Kenmore, WA (US); Richard L. Remmele, Jr., Clarksburg, MD (US)

(73) Assignee: Immunex Corporation, Thousand Oaks, CA (US)

(*) Notice: Subject to any disclaimer, the term of this patent is extended or adjusted under 35 U.S.C. 154(b) by 16 days.

This patent is subject to a terminal disclaimer.

(21) Appl. No.: 14/478,926

(22) Filed: Sep. 5, 2014

(65) Prior Publication Data

US 2014/0377264 A1 Dec. 25, 2014

Related U.S. Application Data

(60) Division of application No. 13/401,496, filed on Feb. 21, 2012, now Pat. No. 8,828,947, which is a continuation of application No. 12/632,690, filed on Dec. 7, 2009, now Pat. No. 8,119,604, which is a division of application No. 11/784,538, filed on Apr. 6, 2007, now Pat. No. 7,648,702, which is a continuation of application No. 10/376,576, filed on Feb. 27, 2003, now abandoned.

(60) Provisional application No. 60/360,257, filed on Feb. 27, 2002.

(51) Int. Cl.
| | |
|---|---|
| C07K 16/18 | (2006.01) |
| A61K 9/00 | (2006.01) |
| A61K 47/18 | (2006.01) |
| C07K 14/705 | (2006.01) |

(52) U.S. Cl.
CPC ............. *C07K 16/18* (2013.01); *A61K 9/0019* (2013.01); *A61K 47/183* (2013.01); *C07K 14/70578* (2013.01); *C07K 2319/30* (2013.01); *Y10S 435/81* (2013.01)

(58) Field of Classification Search
CPC ...................... C07K 2319/30; C07K 2319/32
See application file for complete search history.

(56) References Cited

U.S. PATENT DOCUMENTS

| | | | |
|---|---|---|---|
| 5,580,856 A | 12/1996 | Prestrelski et al. | |
| 5,691,312 A | 11/1997 | Paques | |
| 6,004,555 A | 12/1999 | Thorpe et al. | |
| RE36,755 E | 6/2000 | Smith et al. | |
| 6,171,586 B1 | 1/2001 | Lam et al. | |
| 8,063,182 B1* | 11/2011 | Brockhaus | C07K 14/7151 530/350 |
| 2003/0180253 A1 | 9/2003 | Chen et al. | |
| 2003/0190316 A1 | 10/2003 | Kakuta et al. | |
| 2008/0286280 A1 | 11/2008 | Kallmeyer | |

FOREIGN PATENT DOCUMENTS

| | | |
|---|---|---|
| EP | 0 025 275 A2 | 3/1981 |
| EP | 0 025 321 A2 | 3/1981 |
| EP | 0 025 719 A2 | 3/1981 |
| EP | 1 304 376 A | 10/2000 |
| EP | 1 314 437 A1 | 5/2003 |
| EP | 0 909 564 B1 | 6/2006 |
| WO | WO 97/40850 A1 | 11/1997 |
| WO | WO 00/61177 A1 | 10/2000 |
| WO | WO 00/62790 A2 | 10/2000 |
| WO | WO 01/24814 A1 | 4/2001 |
| WO | WO 01/43773 A1 | 6/2001 |
| WO | WO 01/44472 A1 | 6/2001 |
| WO | WO 01/58473 A1 | 8/2001 |
| WO | WO 01/60397 A1 | 8/2001 |
| WO | WO 02/08417 A1 | 1/2002 |
| WO | WO 02/13860 A1 | 2/2002 |

OTHER PUBLICATIONS

Moreland et al., Treatment of rheumatoid arthritis with a recombinant human tumor necrosis factor receptor (p75)-Fc fusion protein, New England Journal of Medicine, 337:141-147 (1997).*
Cleland, et al., "The Development of Stable Protein Formulations: A Close Look at Protein Aggregation, Deamidation, and Oxidation", Critcal Reviews in Therapeutic Drug Carrier Systems, 10(4):307-377, 1993.
Clinical Pharmacology and Therapeutics, Aug. 1999, vol. 66, No. 2, p. 205-209.
Daugherty et al., "Formulation and delivery issues for monoclonal antibody therapeutics", Advanced Drug Delivery Reviews, 2006, 58: 686-706.
Hora, et al., "Lycophilized Formulations of Recombinant Tumor Necrosis Factor", Pharmaceutical Research, 9(1):33-36, 1992.
Kalden, Joachim R., "Emerging role of anti-tumor necrosis factor therapy in rheumatic diseases", Arthritis Research, 2002, vol. 4, Suppl 2, pp. S34-S40.
Liu, et al., "Moisture-Induced Aggregation of Lycophilized Proteins in the Solid State", Biotechnology and Bioengineering, 37:177-184, 1991.
Maksymowych, Walter P., "Novel therapies in the treatment of spondyloarthritis", Expert Opin. Investig. Drugs, 2002, vol. 11(7), pp. 937-945.
Manning, et al., "Stability of Protein Pharmaceuticals", Pharmaceutical Research, 6(11):903-918, 1989.
Moreland et al. "Etanercept Therapy in Rheumatoid Arthritis. A Randomized, Controlled Trial" Ann Intern Med; 130:478-486, 1999.
Quyyumi, Arshed A., "Does Acute Improvement of Endothelial Dysfunction in Coronary Artery Disease Improve Myocardial Ischemia? A Double-Blind Comparison of Parenteral D- and L-Arginine" Journal of American College of Cardiology, 1998, 32(4): 904-911.
Remmele et al., "Interleukin-1 Receptor (IL-1R) Liquid Formulation Development Using Differential Scanning Calorimetry", Pharmaceutical Research, 1998, vol. 12, No. 2, pp. 200-208.
Rishi et al., "Role of non-compatible osmolytes in the stabilization of proteins during heat stress", Biochemical Journal, 1998, vol. 329, pp. 137-143.
Robbins, et al., "Antibodies to Covalent Aggregates of Insulin in Blood of Insulin-Using Diabetic Patients", Diabetes, 36:838-845, 1987.

(Continued)

*Primary Examiner* — Lorraine Spector
(74) *Attorney, Agent, or Firm* — Nathan Machin

(57) ABSTRACT

The present invention relates to pharmaceutical compositions comprising a p75 tumor necrosis factor receptor/Ig fusion protein.

23 Claims, 12 Drawing Sheets

(56) References Cited

OTHER PUBLICATIONS

Soejima, et al., "An Efficient Refolding Method for the Preparation of Recombinant Human Prethrombin-2 and Characterization of the Recombinant-Derived α-Thrombin", J. Biochem., 130:269-277, 2001.
Supplementary European Search Report, EP 03 71 6244, mailed Jan. 23, 2006.
Wang W. et al., "Antibody Structure, Instability, and Formulation", Journal of Pharmaceutical Sciences, 2007, 96(1) pp. 1-26.
Wang, W., "Instability, stabilization, and formulation of liquid protein pharmaceuticals", Int. J. Pharmaceutics, 185(2):129-188, 1999.
Wang, Y-C.J., et al., "Parenteral Formulations of Proteins and Peptides: Stability and Stabilizers", J Parenteral Science & Technology, 42(2S):S04-S26, 1988.
Yancey et al., Living with Water Stress: Evolution of Osmolyte Systems, Science, 1982, vol. 217, pp. 1214-1222.

* cited by examiner

COMPOSITIONS COMPRISING A P75 TUMOR NECROSIS FACTOR RECEPTOR/IG FUSION PROTEIN

CROSS-REFERENCE TO RELATED APPLICATIONS

This application is a divisional of U.S. Ser. No. 13/401,496, filed Feb. 21, 2012, now U.S. Pat. No. 8,828,947, which is a continuation of U.S. Ser. No. 12/632,690, filed Dec. 7, 2009, now issued as U.S. Pat. No. 8,119,604, which is a divisional of U.S. application Ser. No. 11/784,538, filed Apr. 6, 2007, now issued as U.S. Pat. No. 7,648,702, which is a continuation of U.S. application Ser. No. 10/376,576, filed Feb. 27, 2003, now abandoned, which claims the benefit under 35 U.S.C. 119(e) of U.S. Provisional Application No. 60/360,257, filed Feb. 27, 2002, which is hereby incorporated by reference.

FIELD OF THE INVENTION

The present invention relates to an aqueous pharmaceutical composition suitable for long-term storage of polypeptides containing an Fc domain of an immunoglobulin, methods of manufacture of the composition, methods of administration and kits containing same.

BACKGROUND

After production, polypeptides must typically be stored prior to their use. Frequently, when stored for extended periods polypeptides are unstable in solution (Manning et al., 1989, Pharm. Res. 6:903-918). Accordingly, additional processing steps have been developed to allow for a longer shelf life including drying, e.g., lyophilization. However, lyophilized pharmaceutical compositions are less convenient for the end user.

Typical practices to improve polypeptide stability can be addressed by varying the concentration of elements with the formulation, or by adding excipients to modify the formulation (U.S. Pat. Nos. 5,580,856 and 6,171,586). The use of additives, while improving storage, can still results in inactive polypeptides. In addition, in the case of lyophilization, the rehydration step can introduce conditions that result in inactivation of the polypeptide by, for example, aggregation or denaturation (Hora et al., 1992, Pharm. Res., 9:33-36; Liu et al., 1991, Biotechnol. Bioeng., 37:177-184). In fact, aggregation of polypeptides is undesirable as it may result in immunogenicity (Cleland et al., 1993, Crit. Rev. Therapeutic Drug Carrier Systems, 10:307-377; and Robbins et al., 1987, Diabetes, 36:838-845).

The present invention addresses these issues by providing a novel stable liquid formulation that allows long term storage of a polypeptide containing an Fc domain of an immunoglobulin.

SUMMARY

The invention relates, in part, to a stable aqueous pharmaceutical composition comprising a therapeutically effective amount of an Fc domain containing polypeptide, an aggregation inhibitor selected from the group consisting of L-arginine and L-cysteine. Optionally, the composition can include a buffer, a tonicity modifier and one or more excipients. In one aspect, the buffer maintains the composition pH at a range of about 6.0 and about 7.0. Preferably, the Fc domain containing polypeptide is stable in the present formulation for at least three months at 2-8° C. and/or is stable following one or more freezing and thawing cycles of the formulation.

The invention also relates to a method of formulating a pharmaceutical composition, the composition an Fc domain containing polypeptide with an aggregation inhibitor selected from the group consisting of L-arginine and L-cysteine. Optionally, one can also add to the pharmaceutical composition a buffer, a tonicity modifier and/or an excipient. In one aspect, the pharmaceutical composition is formulated at a pH range between pH 6.0 and 7.0.

The invention also relates to a method of treating a mammal comprising administering a therapeutically effective amount of the pharmaceutical composition described herein, wherein the mammal has a disease or disorder that can be beneficially treated with a Fc domain containing polypeptide in the composition.

The invention also relates to a method of accelerated stability testing of an Fc domain containing polypeptide in a pharmaceutical composition of the invention comprising the steps of storing the composition at 37° C. for one month and measuring the stability of the polypeptide.

In another embodiment, the present invention is directed to a kit or container, which contains an aqueous pharmaceutical composition of the invention. The kit can also be accompanied by instructions for use.

DETAILED DESCRIPTION

Figure 1:
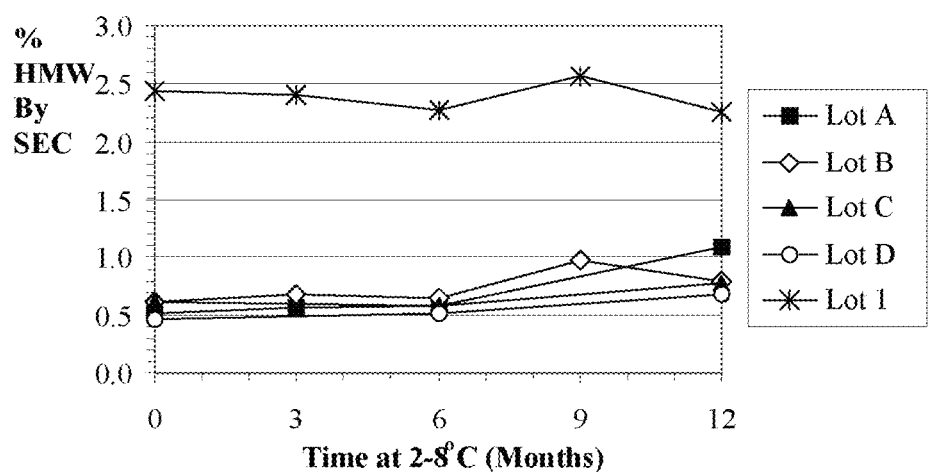
FIG. 1: Size exclusion chromatography (SEC) data for lots A, B, C and D, and lot 1 stored for up to 1 year at 2-8° C.

In long-term storage of pharmaceutical compositions containing polypeptides, including aqueous and lyophilized formulations, active polypeptides can be lost due to aggregation and/or degradation. Thus, the present invention is directed to an aqueous formulation that surprisingly allows for stable long-term storage of a pharmaceutical composition wherein the active ingredient in the composition is a polypeptide having an Fc domain of an antibody. This formulation is useful, in part, because it is more convenient to use for the patient, as this formulation does not require any extra steps such as rehydrating.

As used herein, the phrase "pharmaceutical composition" is understood to refer to a formulation comprised of a polypeptide prepared such that it is suitable for injection and/or administration into a patient in need thereof. More particularly, a pharmaceutical composition is substantially sterile and does not contain any agents that are unduly toxic or infectious to the recipient. Further, it is to be understood that, as used herein, a solution or liquid formulation is meant to mean a liquid preparation that contains one or more chemical substances dissolved in a suitable solvent or mixture of mutually miscible solvents.

In addition, as used herein, the term "about" is understood to mean that there can be variation in the concentration of a component of the described formulation that can be to 5%, 10%, 15% or up to and including 20% of the given value. For example, if a formulation has about 10 mg/ml of an Fc domain containing polypeptide, this is understood to mean that a formulation can have between 8 to 12 mg/ml of the stated polypeptide.

In one embodiment, the formulation is comprised of an Fc domain containing polypeptide, an aggregation inhibitor selected from group consisting of L-arginine and L-cysteine, and, optionally, a buffer, a tonicity modifier and additional excipients as necessary. L-arginine has been used to assist refolding of insoluble polypeptides, particularly those expressed to high levels in inclusion bodies in bacteria. However, L-arginine has not been utilized successfully to enhance stability of Fc domain containing polypeptides in pharmaceutical compositions (Soejima et al., 2001, J. Biochem., 130:369-277).

It is contemplated that the preparation of the composition should be done in consideration of limiting injection site discomfort. It is further contemplated that additional active ingredients can also be included in the presently described composition, for example, to reduce injection site discomfort. Such active ingredients include, but are not limited to non-steroidal anti-inflammatory drugs such as, for example, tromethamine, in an appropriate dosage.

Polypeptides

In a particular embodiment the Fc domain containing polypeptide is a soluble form of the TNF receptor fused to an Fc domain (TNFR:Fc), however, it is to be understood that any polypeptide containing an Fc domain is suitable for use in the instant formulation. A commercially available TNFR:Fc is known as etanercept (Enbrel®, Immunex Corporation), which is a dimeric fusion polypeptide consisting of the extracellular ligand-binding portion of the human 75 kilodalton (p75) tumor necrosis factor receptor (TNFR) linked to the Fc portion of human IgG1. The Fc component of etanercept contains the constant heavy 2 (CH2) domain, the constant heavy 3 (CH3) domain and hinge region, but not the constant heavy 1 (CH1) domain of human IgG1. It is to be understood that an Fc domain can contain one or all of the domains described above. Etanercept is produced by recombinant DNA technology in a Chinese hamster ovary (CHO) mammalian cell expression system. It consists of 934 amino acids and has an apparent molecular weight of approximately 150 kilodaltons (Physicians Desk Reference, 2002, Medical Economics Company Inc.).

Other polypeptides specifically contemplated for formulation according to the invention include recombinant fusion polypeptides comprising at least a portion of an Fc domain of an antibody. A polypeptide fused to an Fc domain and identical to or substantially similar to one of the following polypeptides is suitable for use in the present pharmaceutical composition: a flt3 ligand, a CD40 ligand, erythropoeitin, thrombopoeitin, calcitonin, Fas ligand, ligand for receptor activator of NF-kappa B (RANKL), tumor necrosis factor (TNF)-related apoptosis-inducing ligand (TRAIL), thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS).

Polypeptides suitable for formulation according to the invention also include recombinant fusion polypeptides comprising an Fc domain of an antibody plus a receptor for any of the above-mentioned polypeptides or polypeptides substantially similar to such receptors. These receptors include: both forms of TNFR (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL (TRAIL receptors 1, 2, 3, and 4), and receptors that comprise death domains, such as Fas or Apoptosis-Inducing Receptor (AIR).

Other polypeptides suitable for use in the present formulation include differentiation antigens (referred to as CD polypeptides) or their ligands or polypeptides substantially similar to either of these, which are fused to an Fc domain of an antibody. Such antigens are disclosed in Leukocyte Typing VI (Proceedings of the VIth International Workshop and Conference, Kishimoto, Kikutani et al., eds., Kobe, Japan, 1996). Similar CD polypeptides are disclosed in subsequent workshops. Examples of such antigens include CD27, CD30, CD39, CD40, and ligands thereto (CD27 ligand, CD30 ligand, etc.). Several of the CD antigens are members of the TNF receptor family, which also includes 41BB ligand and OX40. The ligands are often members of the TNF family, as are 41BB ligand and OX40 ligand. Accordingly, members of the TNF and TNFR families can be formulated according to the present invention.

Enzymatically active polypeptides or their ligands can also be formulated according to the invention. Examples include recombinant fusion polypeptides comprising an Fc domain of an antibody fused to all or part of one of the following polypeptides or their ligands or a polypeptide substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands.

The formulations and methods of the invention can also be used to prepare pharmaceutical compositions comprising antibodies, human antibodies, humanized antibodies, chimeric antibodies, i.e. antibodies having human constant antibody immunoglobulin domains coupled to one or more murine variable antibody immunoglobulin domain, and/or non-human antibodies, or fragments thereof. Specific examples of antibodies suitable for use in the present formulation include commercially available antibodies such as muromonab-CD3 (Orthoclone OKT-3®, Ortho Biotech), abciximab (ReoPro®, Lilly), rituximab (Rituxan®, IDEC), daclixmab (Zenapax®, Roche Laboratories), basiliximab (Simulect®, Novartis), infliximab (Remicade®, Centocor), palivizumab (Synagis®, MedImmune), trastuzumab (Herceptin®, Genentech), gemtuzuman ozogamicin (Mylotarg™, Wyeth-Ayerst), and alemtuzumab (Campath®, Berlex). Currently each of the foregoing is available either as a lyophilized powder requiring rehydration or as a concentrate requiring dilution prior to administration. The present formulation obviates the need for any manipulations prior to administration, e.g., rehydrating or dilution, while preserving stability of the active ingredients over long-term storage.

The pharmaceutical composition of the invention can also be used to store polypeptides comprising an antibody conjugated to a cytotoxic or luminescent substance. Such substances include: maytansine derivatives (such as DM1); enterotoxins (such as a Staphylococcal enterotoxins); iodine isotopes (such as iodine-125); technetium isotopes (such as Tc-99m); cyanine fluorochromes (such as Cy5.5.18); and ribosome-inactivating polypeptides (such as bouganin, gelonin, or saporin-S6).

Examples of antibodies or antibody/cytotoxin or antibody/luminophore conjugates contemplated for use in the invention include those that recognize one or more of the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-4, IL-5, IL-8, IL-10, IL-2 receptor, IL-4 receptor, IL-6 receptor, IL-13 receptor, PDGF-β, VEGF, TGF, TGF-β2, TGF-β1, EGF receptor, VEGF receptor, C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or polypeptides expressed on breast, colon, squamous cell, prostate, pancreatic, lung, and/or kidney cancer cells and/or on melanoma, glioma, or neuroblastoma cells, TRAIL receptors 1, 2, 3 and 4, the necrotic core of a tumor, integrin alpha 4 beta 7, the integrin VLA-4, B2 integrins, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IFN-γ, Respiratory Syncitial Virus, human immunodeficiency virus (HIV), hepatitis B virus (HBV), *Streptococcus mutans*, and *Staphylococcus aureus*.

The formulations of the invention can also be used for anti-idiotypic antibodies, or substantially similar polypeptides, including but not limited to anti-idiotypic antibodies against: an antibody targeted to the tumor antigen gp72; an antibody against the ganglioside GD3; or an antibody against the ganglioside GD2.

The Fc domain containing polypeptide suitable for storage in the present pharmaceutical composition can be produced by living host cells that express the polypeptide, such as hybridomas in the case of antibodies, or host cells that that have been genetically engineered to produce the polypeptide in the case of fusion polypeptides or antibodies. Methods of genetically engineering cells to produce polypeptides are well known in the art. See, e.g., Ausubel et al., eds. (1990), Current Protocols in Molecular Biology (Wiley, N.Y.). Such methods include introducing nucleic acids that encode and allow expression of the polypeptide into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and WI38. New animal cell lines can be established using methods well know by those skilled in the art (e.g., by transformation, viral infection, and/or selection). Optionally, the polypeptide can be secreted by the host cells into the medium.

Purification of the expressed Fc domain containing polypeptide can be performed by any standard method. When the Fc domain containing polypeptide is produced intracellularly, the particulate debris is removed, for example, by centrifugation or ultrafiltration. When the polypeptide is secreted into the medium, supernatants from such expression systems can be first concentrated using standard polypeptide concentration filters. Protease inhibitors can also be added to inhibit proteolysis and antibiotics can be included to prevent the growth of microorganisms.

The Fc domain containing polypeptide can be purified using, for example, hydroxyapatite chromatography, gel electrophoresis, dialysis, and affinity chromatography, and any combination of purification techniques known or yet to discovered. For example, protein A can be used to purify Fc domain containing polypeptides that are based on human gamma 1, gamma 2, or gamma 4 heavy chains (Lindmark et al., 1983, J. Immunol. Meth. 62:1-13). Protein G is recommended for all mouse isotypes and for human gamma 3 (Guss et al., 1986, EMBO J. 5:1567-1575).

Other techniques for polypeptide purification such as fractionation on an ion-exchange column, ethanol precipitation, reverse phase HPLC, chromatography on silica, chromatography on heparin SEPHAROSET™, chromatography on an anion or cation exchange resin (such as a polyaspartic acid column), chromatofocusing, SDS-PAGE, and ammonium sulfate precipitation can also be utilized depending on need.

Pharmaceutical Composition

The present pharmaceutical composition is prepared by combining, in addition to a purified polypeptide described above, an aggregation inhibitor. Further, a buffer, a tonicity modifier and an additional excipient can be added as needed. It will be understood one of ordinary skill in the art that the combining of the various components to be included in the composition can be done in any appropriate order, namely, the buffer can be added first, middle or last and the tonicity modifier can also be added first, middle or last. It is also to be understood by one of ordinary skill in the art that some of these chemicals can be incompatible in certain combinations, and accordingly, are easily substituted with different chemicals that have similar properties but are compatible in the relevant mixture.

Aggregation inhibitors reduce a polypeptide's tendency to associate in inappropriate or unwanted ternary or quaternary complexes. Unexpectedly, the present inventors have found that the amino acids L-arginine and/or, L-cysteine, act to reduce aggregation of Fc domain containing polypeptide in a formulation for long periods, e.g., two years or more. The concentration of the aggregation inhibitor in the formulation is preferably between about 1 mM to 1M, more preferably about 10 mM to about 200 mM, more preferably about 10 mM to about 100 mM, even more preferably about 15 mM to about 75 mM, and yet more preferably about 25 mM. These compounds are available from commercial suppliers.

Buffering agents maintain pH in a desired range and various buffers suitable for use in the pharmaceutical composition of the invention include histidine, potassium phosphate, sodium or potassium citrate, maleic acid, ammonium acetate, tris-(hydroxymethyl)-aminomethane (tris), various forms of acetate and diethanolamine. One preferred buffer is sodium phosphate as its buffering capacity is at or near pH 6.2. The concentration of the buffer in the formulation is preferably between about 1 mM to about 1M, more preferably about 10 mM to about 200 mM. Buffers are well known in the art and are manufactured by known methods and available from commercial suppliers.

When the pH of the pharmaceutical composition is set at or near physiological levels comfort of the patient upon administration is maximized. In particular, it is preferred that the pH be within a range of pH about 5.8 to 8.4, with about 6.2 to 7.4 being preferred, however, it is to be understood that the pH can be adjusted as necessary to maximize stability and solubility of the polypeptide in a particular formulation and as such, a pH outside of physiological ranges, yet tolerable to the patient, is within the scope of the invention.

A tonicity modifier is understood to be a molecule that contributes to the osmolality of a solution. The osmolality of a pharmaceutical composition is preferably regulated in order to maximize the active ingredient's stability and also to minimize discomfort to the patient upon administration. Where serum is approximately 300+/−50 milliosmolals per kilogram. It is generally preferred that a pharmaceutical composition be isotonic with serum, i.e., having the same or similar osmolality, which is achieved by addition of a tonicity modifier, thus it is contemplated that the osmolality will be from about 180 to about 420 milliosmolals, however, it is to be understood that the osmolality can be either higher or lower as specific conditions require. Examples of tonicity modifiers suitable for modifying osmolality include, but are not limited to amino acids (e.g., arginine, cysteine, histidine and glycine), salts (e.g., sodium chloride, potassium chloride and sodium citrate) and/or saccharides (e.g., sucrose, glucose and mannitol). The concentration of the tonicity modifier in the formulation is preferably between about 1 mM to 1M, more preferably about 10 mM to about 200 mM. Tonicity modifiers are well known in the art and are manufactured by known methods and available from commercial suppliers.

Excipients, also referred to as chemical additives, co-solutes, or co-solvents, that stabilize the polypeptide while in solution (also in dried or frozen forms) can also be added to a pharmaceutical composition. Examples include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), dextran, PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols, (e.g., PEG, ethylene glycol and glycerol) dimethysulfoxide (DMSO) and dimethylformamide (DMF); amino acids such as: proline, L-serine, sodium glutamic acid, alanine, glycine, lysine hydrochloride, sarcosine and gamma-aminobutyric acid; surfactants such as: Tween-80™ (polysorbate 80), Tween-20™ (polysorbate 20), SDS, polysorbate, polyoxyethylene copolymer; and miscellaneous excipients such as: potassium phosphate, sodium acetate, ammonium sulfate, magnesium sulfate, sodium sulfate, trimethylamine N-oxide, betaine, metal ions (e.g., zinc, copper, calcium, manganese, and magnesium), CHAPS, monolaurate, 2-O-beta-mannoglycerate or any combination of the above.

The concentration of one or more excipients in a formulation of the invention is/are preferably between about 0.001 to 5 weight percent, more preferably about 0.1 to 2 weight percent. Excipients are well known in the art and are manufactured by known methods and available from commercial suppliers.

In one illustrative embodiment, a formulation of the invention can comprise about 25 to about 50 mg TNFR:Fc (etanercept), about 10 mM to about 100 mM L-arginine, about 10 mM to about 50 mM sodium phosphate, about 0.75% to about 1.25% sucrose, about 50 mM to about 150 mM NaCl, at about pH 6.0 to about pH 7.0. In another embodiment L-arginine can be replaced with L-cysteine (at about 1 to about 500 micromolar) in the formulation. In yet another embodiment, the pH can be about pH 7.0. In another specific embodiment, a formulation of the invention can comprise about 25 mg/ml TNFR:Fc, about 25 mM L-arginine, about 25 mM sodium phosphate, about 98 mM sodium chloride, and about 1% sucrose at about pH 6.2.

In another embodiment, a formulation of the invention can comprise about 10 to about 100 mg/mL of RANK:Fc in about 10 mM to about 100 mM L-arginine, about 10 mM to about 50 mM sodium phosphate, about 0.75% to about 1.25% sucrose, about 50 mM to about 150 mM NaCl, at about pH 6 to about pH 7. In a specific embodiment, the formulation of the invention comprises 50 mg/ml RANK:Fc in about 25 mM L-arginine, about 25 mM sodium phosphate, about 98 mM sodium chloride, and about 1% sucrose at about pH 6.2.

In yet another embodiment, a formulation of the invention can comprise an effective amount of an Fc domain containing polypeptide, about 10 mM to about 100 mM L-arginine, about 10 mM to about 50 mM sodium phosphate, about 0 to 5% Mannitol and 0 to 0.2% Tween-20™ (polysorbate 20) at about pH 6 to 7. In another embodiment, a formulation of the invention can comprise an effective amount of an antibody, such as Emab (an anti-CD22 specific antibody), about 25 mM L-arginine, about 25 mM sodium phosphate, about 4% Mannitol, about 0.02% Tween-20™ (polysorbate 20) and at about pH 6.0.

In yet another embodiment, the invention provides a method of treating a mammal comprising administering a therapeutically effective amount of the pharmaceutical composition described herein, wherein the mammal has a disease or disorder that can be beneficially treated with a Fc domain containing polypeptide in the composition. In yet another embodiment, the Fc domain containing polypeptide is derived from the same species of mammal as is to be treated with the composition. In a particular embodiment, the mammal is a human patient in need of treatment. When the Fc domain containing polypeptide of the composition is TNFR:Fc, examples of diseases or disorders that can be treated include but are not limited to rheumatoid arthritis, psoriatic arthritis, ankylosing spondylitis, Wegener's disease (granulomatosis), Crohn's disease (or inflammatory bowel disease), chronic obstructive pulmonary disease (COPD), Hepatitis C, endometriosis, asthma, cachexia, psoriasis, and atopic dermatitis. Additional diseases or disorders that can be treated with TNFR:Fc include those described in WO 00/62790, WO 01/62272 and U.S. Patent Application No. 2001/0021380, the relevant portions of which are incorporated herein by reference.

In yet another embodiment, the invention provides a method for accelerated stability testing of the stability an Fc domain containing polypeptide in a pharmaceutical composition of the invention comprising the steps of testing the activity of the polypeptide formulated according to the invention prior to storage, i.e., time zero, storing the composition at 37° C. for one month and measuring the stability of the polypeptide, and comparing the stability form time zero to the one month time point. This information is helpful for early elimination of batches or lots that appear to have good stability initially, yet do not store well for longer periods.

Moreover, the present pharmaceutical composition provides improved long-term storage such that the active ingredient, e.g., an Fc domain containing polypeptide, is stable over the course of storage either in liquid or frozen states. As used herein, the phrase "long-term" storage is understood to mean that the pharmaceutical composition can be stored for three months or more, for six months or more, and preferably for one year or more. Long term storage is also understood to mean that the pharmaceutical composition is stored either as a liquid at 2-8° C. or is frozen, e.g., at −20° C. or colder. It is also contemplated that the composition can be frozen and thawed more than once. The term "stable" with respect to long-term storage is understood to mean that the active polypeptide of the pharmaceutical composition does not lose more than 20%, or more preferably 15%, or even more preferably 10%, and most preferably 5% of its activity relative to activity of the composition at the beginning of storage.

Effective Dose of the Pharmaceutical Composition

The appropriate dosage, or therapeutically effective amount, of the Fc domain containing polypeptide of the formulation will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations. The pharmaceutical composition can be administered as a sole therapeutic or in combination with additional therapies as needed.

In one embodiment, the effective Fc domain containing polypeptide amount per adult dose ranges from about 1-500 mg/m$^2$, or from about 1-200 mg/m$^2$, or from about 1-40 mg/m$^2$ or about 5-25 mg/m$^2$. Alternatively, a flat dose may be administered, whose amount may range from 2-500 mg/dose, 2-100 mg/dose or from about 10-80 mg/dose. If the dose is to be administered more than one time per week, an exemplary dose range is the same as the foregoing described dose ranges or lower and preferably administered two or more times per week at a per dose range of 25-100 mg/dose. In another embodiment, an acceptable dose for administration by injection contains 80-100 mg/dose, or alternatively, containing 80 mg per dose. The dose can be administered at biweekly, weekly doses, or separated by several weeks (for example 2 to 8). In this example TNFR: Fc (etanercept) is generally administered at 25 mg by a single subcutaneous (SC) injection.

In many instances, an improvement in a patient's condition will be obtained by a dose of up to about 100 mg of the pharmaceutical composition one to three times per week over a period of at least three weeks, though treatment for longer periods may be necessary to induce the desired degree of improvement. For incurable chronic conditions the regimen may be continued indefinitely. For pediatric patients (ages 4-17), a suitable regimen involves a dose of 0.4 mg/kg to 5 mg/kg of a the polypeptides of the invention, administered one or more times per week.

In another embodiment, it is contemplated that the pharmaceutical formulation of the invention is prepared in a bulk formulation and as such, the components of the pharmaceutical composition are adjusted so that it is higher than would be required for administration and diluted appropriately prior to administration.

Administration of the Pharmaceutical Composition

The pharmaceutical compositions of this invention are particularly useful for parenteral administration, i.e., subcutaneously, intramuscularly, intravenously, intraperitoneal, intracerebrospinal, intra-articular, intrasynovial, and/or intrathecal. Parenteral administration can be by bolus injection or continuous infusion. Pharmaceutical compositions for injection may be presented in unit dosage form, e.g., in ampoules or in multi-dose containers, with an added preservative. In addition, a number of recent drug delivery approaches have been developed and the pharmaceutical compositions of the present invention are suitable for administration using these new methods, e.g., Inject-Ease™, Genject™, injector pens such as GenPen™, and needleless devices such as MediJector™ and BioJector™. The present pharmaceutical composition can also be adapted for yet to be discovered administration methods. See also Langer, 1990, Science, 249:1527-1533.

The pharmaceutical composition can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. The syringe can be accompanied by instructions for administration.

In another embodiment, the present invention is directed to a kit or container, which contains an aqueous pharmaceutical composition of the invention. The concentration of the polypeptide in the aqueous pharmaceutical composition can vary over a wide range, but is generally within the range of from about 0.05 to about 20,000 micrograms per milliliter (µg/ml) of aqueous formulation. The kit can also be accompanied by instructions for use.

The invention will be more fully understood by reference to the following examples. The examples should not, however, be construed as limiting the scope of the invention.

EXAMPLES

Example 1

In order to determine the best excipient to prevent aggregation of an Fc domain containing polypeptide, TNFR:Fc was produced and tested for light scattering of a sample (Is) containing the TNFR:Fc with various excipients after incubation at 51° C.+/−1° C., and compared to light scattering of a control (Ic) sample with TNFR:Fc alone stored at 2-8° C.

The ratio is measured as Is/Ic, and a ratio of one represents a theoretical baseline where there is no change in the light scattering, i.e., aggregation, of the test compound. The various excipients tested included 5% ascorbic acid, 5% mannitol, 10% sucrose, 1% polyvinylpyrrolidone (PVP-K15), 0.1% polyethylene glycol (PEG, Mw=1000), 0.6% ethanol, 1.2% glycine, 2% L-arginine, 0.01% Pluronic F68, 1.6% Betaine and 1.5% L-cysteine. Surprisingly, L-arginine was the only aggregation inhibitor found to keep the Is/Ic ratio below one for the entire 200 hour test period.

Example 2

TNFR:Fc produced and denoted as lots A, B, C and D were evaluated against TNFR:Fc produced by a different method and having higher initial aggregation (lot 1) for stability in a liquid formulation (25 mM phosphate, 25 mM L-arginine, 98 mM NaCl, 1% sucrose, at pH 6.2) in syringes or glass vials at −70° C., −20° C., 2-8° C., 30° C., and 37° C. Samples were analyzed by size exclusion chromatography (SEC), denatured SEC (dSEC), hydrophobic interaction chromatography (HIC), sodium dodecylsulfate polyacrylamide gel electrophoresis (SDS-PAGE), and for binding and bioactivity at various timepoints. The bioactivity can be measured by any number of assays including by SEC, dSEC, HIC, binding activity and bioactivity, as discussed below.

Figure 2:
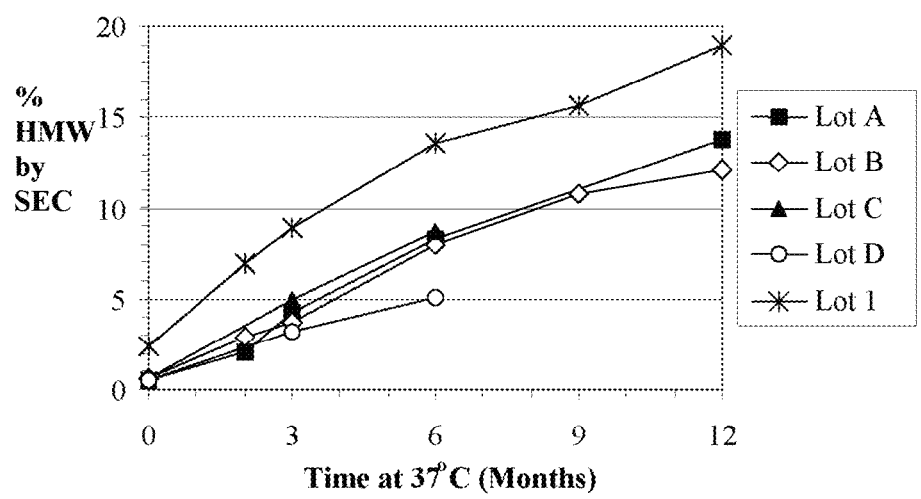
FIG. 2: SEC data for lots A, B, C and D, and lot 1 stored for up to 1 year at 37° C.

Size Exclusion Chromatography:

SEC was used to assess the level of high molecular weight (HMW) species (aggregate that formed) in the samples during storage. Low molecular weight (LMW) species are better resolved by dSEC and that data can be found in the next section. FIG. 1 shows the SEC data for the samples stored at 2-8° C. and FIG. 2 shows the SEC data for samples stored under accelerated conditions of 37° C.

Data was also collected for samples stored at 30° C. (data not shown) and the levels of HMW species were intermediate to those seen at 2-8° C. and 37° C. During storage for 1 year at 2-8° C., aggregate levels remained stable, or increased less than 0.6% in the worst case for lot A. No significant increases in aggregate were seen during storage at 2-8° C. Under accelerated conditions during storage at 37° C., aggregate levels in lot 1 increased to 19% during 12 months, and to 14% and 12% in lot A and B, respectively. The slope of the lines were very similar, showing that the molecules aggregated at the same rate, and that the differences between lots A-D and lot 1 are due to the initial levels of aggregate, higher in lot 1 than lots A-D. For lot B, there was no difference between samples stored in a vial at −70° C., in a syringe at −70° C., in a syringe at −20° C., or in a syringe after thermal treatment and storage at −20° C. (data not shown). All values were within 0.4% of the −70° C. vial control (and the time 0 value) after 12 months of storage.

Figure 3:
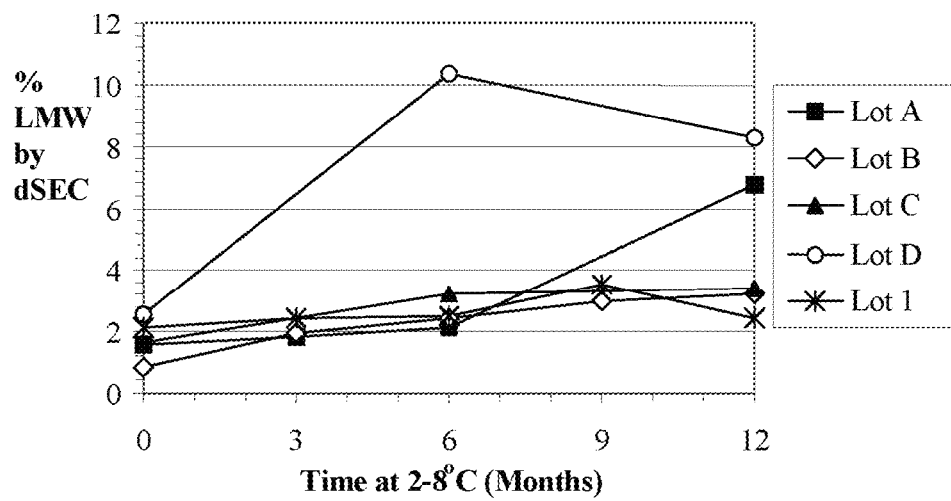
FIG. 3: Denatured SEC (dSEC) data for lots A, B, C and D, and lot 1 stored for up to 1 year at 2-8° C.
Figure 4:
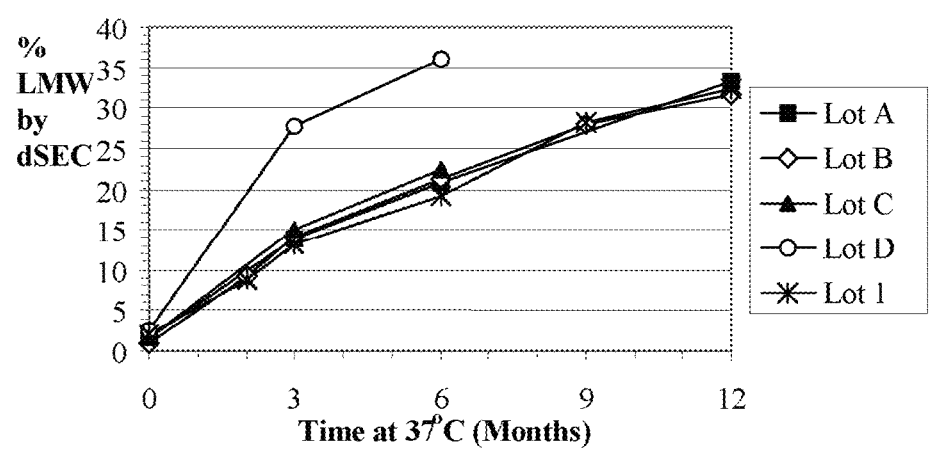
FIG. 4: dSEC data for lots A, B, C and D, and lot 1 stored for up to 1 year at 37° C.

Denatured Size Exclusion Chromatography:

Denatured SEC (dSEC) quantitation of the low molecular weight (LMW) species is shown in FIG. 3 for samples stored at 2-8° C., and FIG. 4 for samples stored at 37° C. Lots A-D and lot 1 were analyzed by dSEC after storage for up to 1 year at 2-8° C., but lots C and D were not analyzed past 6 months of storage under the accelerated conditions of 37° C. During storage at 37° C., lot 1 and lots A, B, and C showed similar breakdown, while lot D showed higher breakdown during heat stressing than lot 1 and the other lots. The similarity in lots A and B and lot 1 was also seen during storage at 30° C. (data not shown), with levels of breakdown intermediate to that seen at 2-8° C. and 37° C. For lot B, there was no difference between samples stored in a vial at −70° C., in a syringe at −70° C., in a syringe at −20° C., or in a syringe after thermal treatment and storage at −20° C. (data not shown). All values after 12 months of storage at −70° C. and −20° C. were within 0.7% of each other and the time 0 value.

During storage at 30° C. (data not shown), the % LMW by dSEC for lot A tracks well with lot B, although both lots show slightly higher levels of breakdown than lot 1 at this temperature. Lot D shows higher levels of LMW species at both 2-8° C. and 37° C. at all timepoints, including time 0. The breakdown products in lot D appear to be larger in size than is typically seen by dSEC analysis of stressed TNFR:Fc samples. These different species are seen after storage at both 2-8° C. and 37° C.

Hydrophobic Interaction Chromatography:

HIC was used to separate various TNFR:Fc-related species. Peak 1 (and an earlier eluting peak denoted as pre-peak 1) has been shown to consist mainly of low molecular weight species. Peak 2 includes the folded, intact dimer (active). Peak 3 includes aggregated material and less active dimers.

Figure 5:
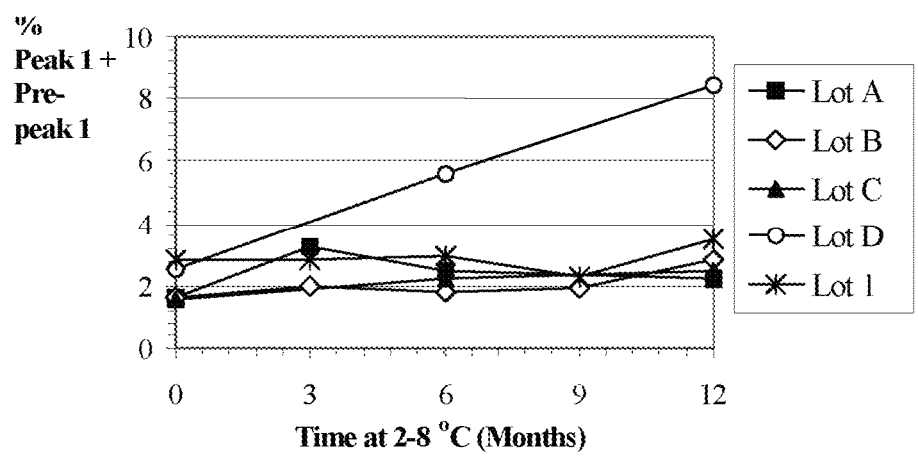
FIG. 5: Hydrophobic interaction chromatography (HIC) Peak 1 and Pre-peak 1 data for lots A, B, C and D, and lot 1 stored for up to 1 year at 2-8° C.
Figure 6:
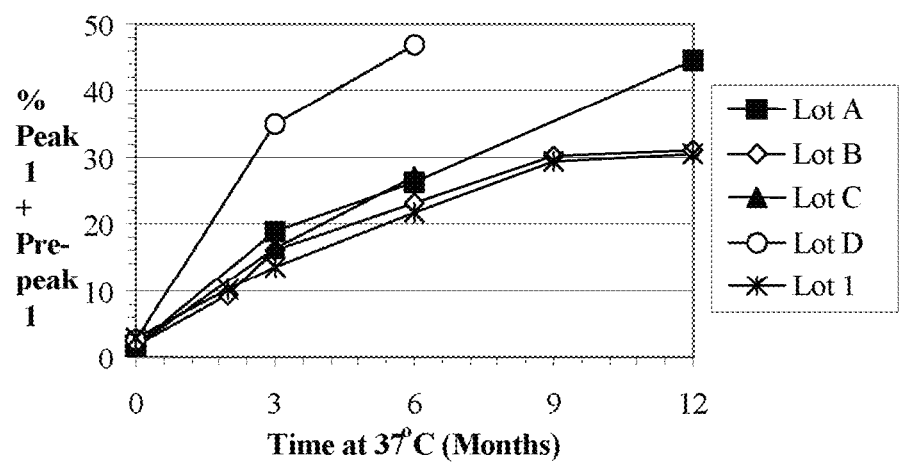
FIG. 6: HIC Peak 1 and Pre-peak 1 data for lots A, B, C and D, and lot 1 stored for up to 1 year at 37° C.

HIC peak 1 data are shown in FIG. 5 for samples stored at 2-8° C. and FIG. 6 for samples stored at 37° C. For all lots except lot D, levels of LMW species remains relatively constant (within 1.2% over 12 months) for samples stored at 2-8° C. If the average value for the −70° C. samples is used in place of the time 0 value for lot A, the curves for all lots except lot D align well. Lot D shows more peak 1 than the other lots, corroborating the high levels of LMW species seen by dSEC. After heat stressing the samples at 37° C. for up to 1 year, lot B and lot 1 show approximately 30% HIC peak 1, whereas lot A shows approximately 45% HIC peak 1. Lot D showed 47% HIC peak 1 after only 6 months of stressing at 37° C.

Figure 7:
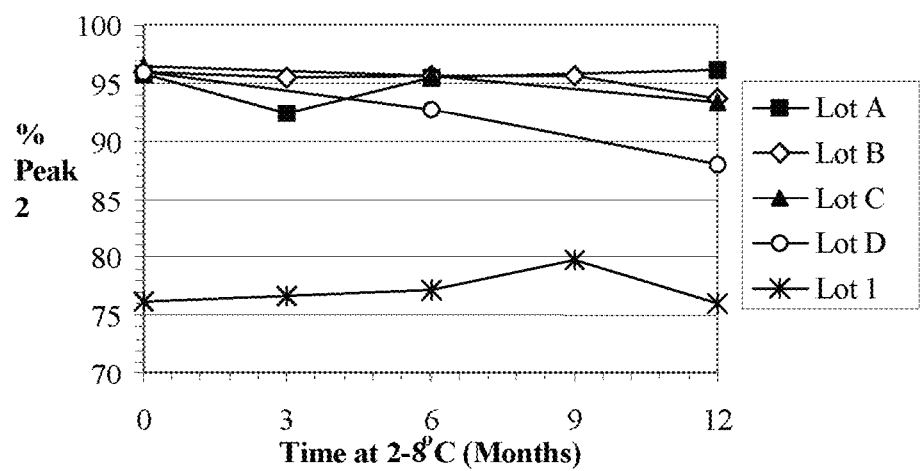
FIG. 7: HIC Peak 2 data for lots A, B, C and D, and lot 1 stored for up to 1 year at 2-8° C.
Figure 8:
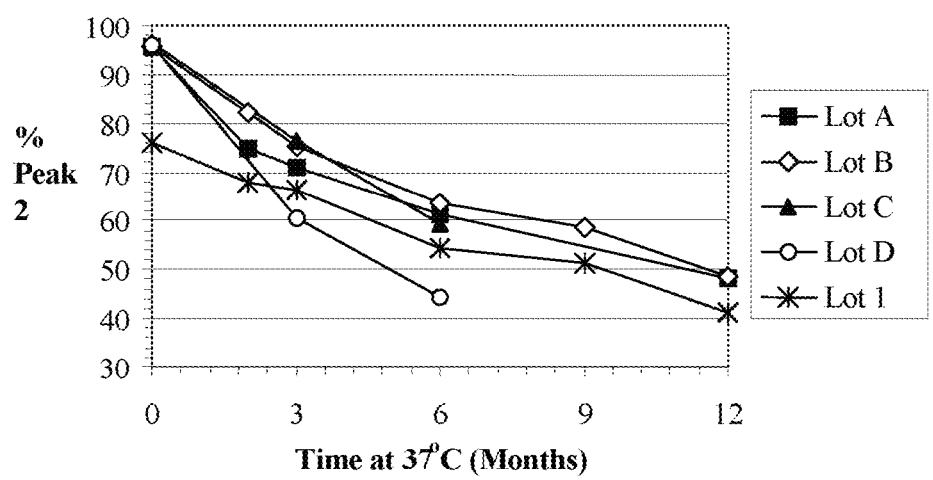
FIG. 8: HIC Peak 2 data for lots A, B, C and D, and lot 1 stored for up to 1 year at 37° C.

As noted above, HIC peak 2 represents the most desired, active species. FIGS. 7 and 8 show the % HIC peak 2 for samples stored at 2-8° C. and 37° C., respectively. Although lot 1 starts out at a lower initial % peak 2, it retains the level of active species during storage for 12 months at 2-8° C. Lots A, B, and C also retain active species during the 12 months of refrigerated storage. Under accelerated conditions of 37° C., all lots tested lose HIC peak 2 during storage.

Figure 9:
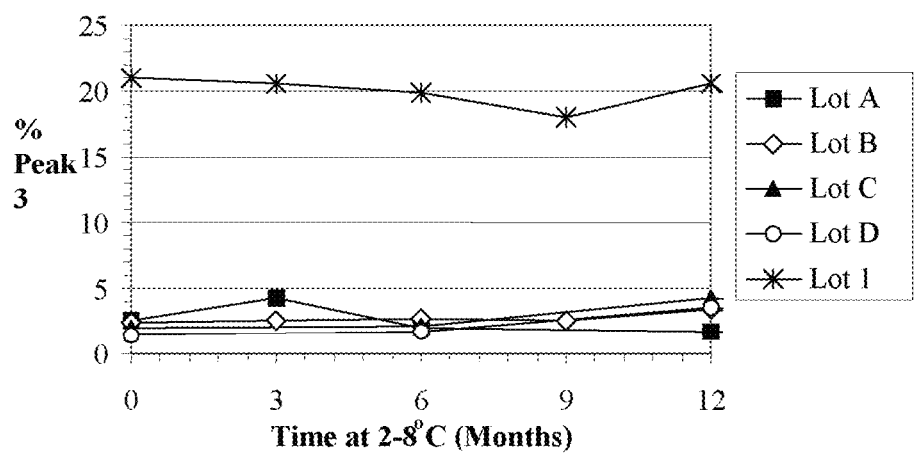
FIG. 9: HIC Peak 3 data for lots A, B, C and D, and lot 1 stored for up to 1 year at 2-8° C.
Figure 10:
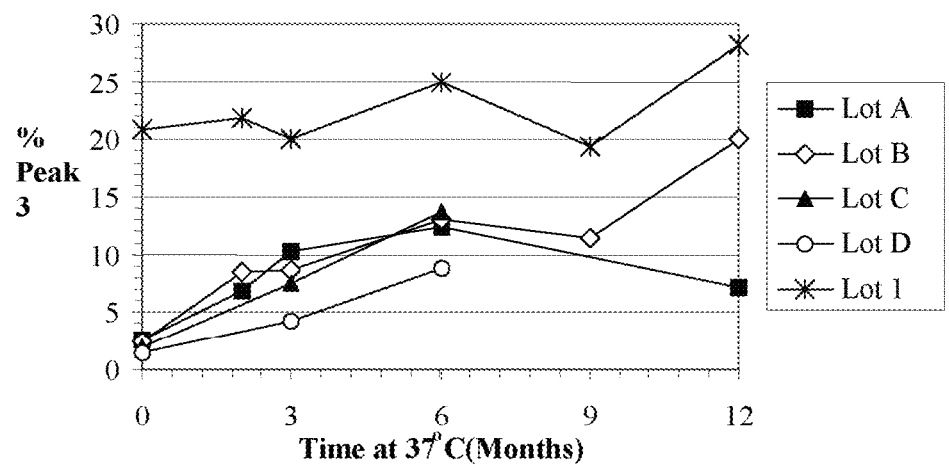
FIG. 10: HIC Peak 3 data for lots A, B, C and D, and lot 1 stored for up to 1 year at 37° C.
Figure 11:
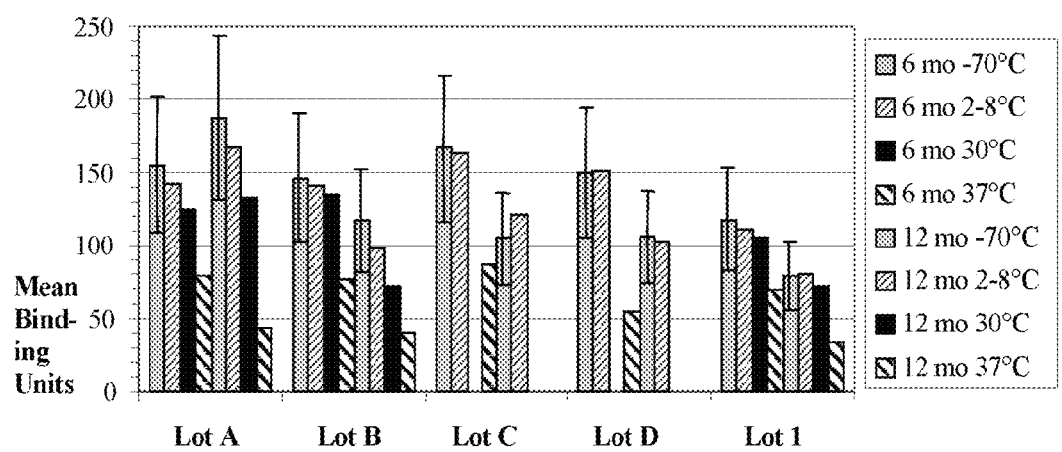
FIG. 11: Binding activity of lots A, B, C and D, and lot 1 stored for 12 months at −70, 2-8, 30, and 37° C.

HIC peak 3 levels remained essentially constant during 1 year of storage at 2-8° C. (FIG. 9). Variation in % peak 3 for all lots ranged between 1 and 3%, well within the error of integration. For lots A, B, C and D, HIC peak 3 does not show baseline resolution, introducing more variability in integration. For lot 1, the peak is more clearly defined. After storage at 37° C., the HIC peak 3 levels in lot 1 are more variable, but remain fairly constant, except for a possible increase at 12 months (FIG. 11). Between lots A-D, no clear differences were seen after storage at 37° C., except for at 12 months, where lot B shows an increase in HIC peak 3 level.

Sodium DodecylSulfate-PolyAcrylamide Gel Electrophoresis:

SDS-PAGE analysis of samples stored for 12 months at −70° C., −20° C., 2-8° C., 30° C., and 37° C. was performed. Lot A had an increase in bands associated with both a ~50 kD and ~34 kD breakdown fragment after storage at 2-8° C. for 1 year. At elevated temperatures, extensive degradation was seen, with many small molecular weight bands showing increased intensities.

Lot 1 showed no change after 1 year of storage at 2-8° C., but showed increased ~50 kD and ~34 kD breakdown fragment after 1 year at 30 and 37° C. Lot B showed no changes during storage for 12 months at −70° C. (vial or syringe) or in syringes at −20° C., with or without thermal treatment to eliminate supercooling. After 12 months at 2-8°

C., however, bands corresponding to both the ~50 kD and ~34 kD breakdown fragment fragments showed increased intensity. Storage at 30 or 37° C. for 1 year resulted in breakdown, with many small molecular weight bands in addition to the previously discussed ~50 kD and ~34 kD breakdown fragment.

Lots C and D were analyzed after storage for 12 months at −70° C. and 2-8° C. Lot 1, and lots B, C and D are were analyzed after storage for 12 months at −70° C. and 2-8° C. and showed similar patterns of degradation as noted above.

Binding and Bioactivity:

FIG. 11 shows the binding activity data derived from an ELISA, for lots A-D and lot 1 stored for 6 and 12 months at −70° C., 2-8° C., 30° C., and 37° C. The error bars on the −70° C. samples indicate +/−30%. Only values outside of these error bars will be considered significant due to assay variability. Lots A and B retained full binding activity after 6 months at 2-8 and 30° C., but at 12 months, only the samples stored at 2-8° C. maintained full binding activity. Lot 1 was able to maintain full activity for up to 12 months after storage at both 2-8 and 30° C., despite showing LMW levels of 13.6% (by dSEC; data not shown) and 8% HMW (by SEC; data not shown) after 1 year at 30° C. Lots C and D also retained full binding activity after 1 year of storage at 2-8° C., despite higher levels of breakdown products seen in lot D by dSEC and HIC.

Figure 12:
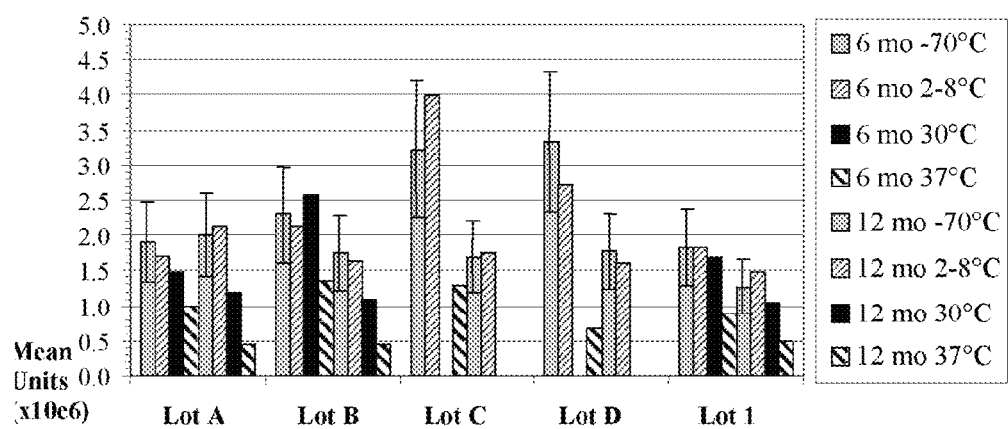
FIG. 12: Bioactivity of lots A, B, C and D, and lot 1 stored for 12 months at −70, 2-8, 30, and 37° C.

An example of a TNFR:Fc bioassay is to inhibit the negative growth response of a cell line to human TNF-alpha. The presence of TNF-alpha inhibits the cells from growing through induction of apoptosis. The presence of biologically active soluble rhuTNF receptor (TNFR:Fc) specifically neutralizes TNF-alpha in a dose-dependent manner. A TNFR reference standard, control, and samples are added and titrated in a 96 well microtiter plate format. A known concentration of cells is added to each well followed by addition of TNF-alpha. After an incubation period, non-adherent cells are removed by gently washing with phosphate buffered saline (PBS) and the remaining cells are stained. After an incubation period, each well is read. The units of each well are directly proportional to the specific activity of TNFR. The results for the bioactivity assay (FIG. 12) corroborate the binding assay data.

Conclusions:

Lots B and C formulated in a liquid phosphate formulation (25 mM phosphate, 25 mM L-arginine, 98 mM NaCl, 1% sucrose, pH 6.2) were shown to be as stable as lot 1 in the same formulation for 1 year at −70° C. or 2-8° C. Lots A-D showed less aggregation than lot 1, and were equivalent in terms of breakdown into lower molecular weight species (less than 4% LMW by dSEC at 12 months). Both lot 1 and the lots A-D showed increased breakdown and aggregation at elevated temperatures of 30 and 37° C., but the lots that performed equal to lot 1 for up to one year at 2-8° C. showed equivalence to lot 1 during heat stressing for 1 year. Lot D was shown to be less stable in the accelerated assay with high levels of low molecular weight breakdown products.

The data from the accelerated stability testing at 30 and 37° C. corresponds with the long-term stability at 2-8° C., and hence provides a method to accelerate the testing of the long-term stability of a formulated polypeptide at low temperatures without requiring a long-term stability assessment. Samples of lot B stored frozen in syringes at −70° C. and −20° C. showed similar stability to samples stored frozen in a vial at −70° C., supporting the use of an embodiment of a pre-filled syringe stored frozen until delivery to the patient.

EQUIVALENTS AND REFERENCES

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A pharmaceutical composition comprising a polypeptide that is an extracellular ligand-binding portion of a human p75 tumor necrosis factor receptor fused to the Fc region of a human IgG1 and from about 10 mM to about 200 mM L-arginine.

2. The pharmaceutical composition of claim 1, wherein the composition is in a liquid state.

3. The pharmaceutical composition of claim 2, wherein the composition is in a pre-filled sterile syringe.

4. The pharmaceutical composition of claim 1, further comprising a buffer.

5. The pharmaceutical composition of claim 4, wherein the buffer is selected from the group consisting of sodium phosphate, histidine, potassium phosphate, sodium citrate, potassium citrate, maleic acid, ammonium acetate, tris-(hydroxymethyl)-aminomethane (tris), acetate and diethanolamine.

6. The pharmaceutical composition of claim 1, further comprising a tonicity modifier.

7. The pharmaceutical composition of claim 6, wherein the tonicity modifier is selected from the group consisting of arginine, cysteine, histidine, glycine, sodium chloride, potassium chloride, sodium citrate, sucrose, glucose and mannitol.

8. The pharmaceutical composition of claim 7, wherein the tonicity modifier is sodium chloride.

9. The pharmaceutical composition of claim 1, further comprising an excipient.

10. The pharmaceutical composition of claim 7, further comprising an excipient.

11. The pharmaceutical composition of claim 9, wherein the excipient is selected from the group consisting of sucrose, lactose, glycerol, xylitol, sorbitol, Mannitol, maltose, inositol, trehalose, glucose, bovine serum albumin (BSA), human SA or recombinant HA, dextran, PVA, hydroxypropyl methylcellulose (HPMC), polyethyleneimine, gelatin, polyvinylpyrrolidone (PVP), hydroxyethylcellulose (HEC), polyethylene glycol, ethylene glycol, glycerol, dimethysulfoxide (DMSO), dimethylformamide (DMF), proline, L-serine, sodium glutamic acid, alanine, glycine, lysine hydrochloride, sarcosine, gamma-aminobutyric acid, polysorbate-20, polysorbate-80, SDS, polysorbate, polyoxyethylene copolymer, potassium phosphate, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate, and 2-O-beta-mannoglycerate.

12. The pharmaceutical composition of claim 11, wherein the excipient is sucrose.

13. A pharmaceutical composition comprising about 10 mg/ml to about 100 mg/ml of a polypeptide that is an extracellular ligand-binding portion of a human p75 tumor necrosis factor receptor fused to the Fc region of a human IgG1, about 10 mM to about 200 mM L-arginine, and sodium phosphate, sodium chloride and sucrose.

14. The pharmaceutical composition of claim 13, wherein the L-arginine is at about 10 mM to about 75 mM.

15. The pharmaceutical composition of claim 13, wherein the sodium phosphate is at about 5 mM to about 100 mM.

16. The pharmaceutical composition of claim 13, wherein the sucrose is at about 0.5% to about 1.5%.

17. The pharmaceutical composition of claim 13, wherein the pH is about 5.5 to about 7.8.

18. The pharmaceutical composition of claim 13, having about 50 mg/ml of the polypeptide that is an extracellular ligand-binding portion of a human p75 tumor necrosis factor receptor fused to the Fc region of a human IgG1, about 25 mM L-arginine, about 25 mM sodium phosphate, about 98 mM sodium chloride, about 1% sucrose, and wherein the composition is about pH 6.2.

19. The pharmaceutical composition of claim 1, wherein the polypeptide is etanercept.

20. The pharmaceutical composition of claim 4, wherein the polypeptide is etanercept.

21. The pharmaceutical composition of claim 6, wherein the polypeptide is etanercept.

22. The pharmaceutical composition of claim 9, wherein the polypeptide is etanercept.

23. The pharmaceutical composition of claim 13, wherein the polypeptide is etanercept.

\* \* \* \* \*